US00PP27792P2

(12) United States Plant Patent
Bacon

(10) Patent No.: US PP27,792 P2
(45) Date of Patent: Mar. 21, 2017

(54) GRAPEVINE PLANT NAMED 'SUGARFORTYSEVEN'

(50) Latin Name: *Vitis vinifera*
Varietal Denomination: Sugarfortyseven

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 14/757,379

(22) Filed: Dec. 22, 2015

(51) Int. Cl.
*A01H 5/08* (2006.01)

(52) U.S. Cl.
USPC ..... Plt./205

(58) Field of Classification Search
USPC ..... Plt./205
See application file for complete search history.

*Primary Examiner* — Annette Para
(74) *Attorney, Agent, or Firm* — Knobbe, Martens, Olson & Bear, LLP

(57) ABSTRACT

A new and distinct grapevine variety 'Sugrafortyseven' is characterized by an early harvest date, the production of a large-sized, red, globose berry and a large bunch size. The berries of 'Sugrafortyseven' are very firm. The new variety 'Sugrafortyseven' is characterized by a higher cluster weight and berry weight compared to 'Flame Seedless' (unpatented). The new variety has similar berry color to the variety 'Crimson Seedless' (unpatented) but begins ripening earlier.

1 Drawing Sheet

Latin name of the genus and species claimed: *Vitis vinifera.*

Variety denomination: 'SUGRAFORTYSEVEN'.

BACKGROUND AND SUMMARY OF THE INVENTION

This invention relates to the discovery and asexual propagation of a new and distinct variety of grapevine, 'Sugrafortyseven', as herein described and illustrated. The new variety was first selected as breeder number 'GR305R' by Terry A. Bacon in Wasco, Kern County, Calif. in July 2012. The variety was originated by controlled hybridization.

The new variety 'Sugrafortyseven' is characterized by an early harvest date, the production of a large-sized, red, globose berries, and a large bunch size. The berries of 'Sugrafortyseven' are very firm with a crisp texture.

The seed parent is the varietal selection 'Sugrathirtyeight' (U.S. Plant Pat. No. 22,431) and the pollen parent is an unpatented breeding selection ('02031-176-252'). The parent varieties were first crossed in May 2010. The date of first sowing was March 2011, and the date of first flowering was May 2012.

The new variety 'Sugrafortyseven' was first asexually propagated in December 2012 in Wasco, Kern County, Calif., by Terry A. Bacon using hardwood cuttings.

The new variety 'Sugrafortyseven' is similar to its seed parent 'Sugrathirtyeight' (U.S. Plant Pat. No. 22,431) in that both varieties have a similar berry color, but they differ in that the new variety 'Sugrafortyseven' has a ripening time of about July 9$^{th}$ compared to August 3$^{rd}$ for 'Sugrathirtyeight' (U.S. Plant Pat. No. 22,431).

The new variety 'Sugrafortyseven' is similar to its pollen parent, unpatented breeding selection '02031-176-252', in that both varieties have a similar ripening time. The new variety differs from its pollen parent in that the new variety 'Sugrafortyseven' has a berry that is red in color while '02031-176-252' has a green berry.

The berry color of the new variety 'Sugrafortyseven' resembles the variety 'Flame Seedless' (unpatented) in appearance. However, the cluster weight of the new variety is about 700 g and berry weight is about 7.8 g, while the cluster weight of 'Flame Seedless' is about 550 g and berry weight is about 5 g. The new variety has similar berry color as the variety 'Crimson Seedless' (unpatented). However, the new variety begins ripening around July 9th, compared to August 28th for 'Crimson Seedless'. The new variety ripens in a similar window as the variety 'Summer Royal' (unpatented), and the two varieties have a similar berry shape. However, the berry of 'Summer Royal' is black while the berry color of the new variety 'Sugrafortyseven' is red.

The new 'Sugrafortyseven' variety has been shown to maintain its distinguishing characteristics through successive asexual propagations by, for example, cuttings and grafting.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration shows typical specimens of the foliage and fruit of the present new grape variety 'Sugrafortyseven'.

The illustration shows the upper and lower surface of the leaves and exterior and sectional views of the fruit.

The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, 1986.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to 'Sugrafortyseven' plants grown in the vicinity of Wasco, Kern County, Calif. during 2015, and is believed to apply to plants of the variety grown under similar conditions of soil and climate elsewhere.

VINE

General: (Measurements taken on a four year old plant).

- *Vine size*.—Medium. Height: Approximately 2.0 m. Width: Approximately 2.2 m.
- *Vigor*.—Medium-low.
- *Density of foliage*.—Medium.
- *Productivity*.—Very productive.
- *Crop load*.—Approximately 28 kg per vine after thinning.
- *Own root*.—Yes.
- *Resistance*.—Neither resistance nor susceptibility to diseases or pests has been observed in this variety.

Trunk:

- *Shape*.—Stocky.
- *Diameter*.—Approximately 7.2 mm (at 30 cm above the soil line).
- *Straps*.—Short.
- *Surface texture*.—Medium smooth.
- *Inner and outer bark color*.—About Light Greyed-Orange 168D to Medium Greyed-Orange 168C.

SHOOTS

Young shoot:

- *Form of tip*.—Half open.
- *Intensity of anthocyanin coloration of tip*.—Absent or very weak.
- *Density of prostrate hairs on tip*.—Sparse.
- *Density of erect hairs on tip*.—Absent or very sparse.
- *Color*.—About Light Green 138D.

Woody shoot (observations made in the middle third of shoot):

- *Attitude before tying*.—Semi-drooping.
- *Growth of axillary shoots*.—Weak, mainly 14 to 16 cm.
- *Internode length*.—Medium, Approximately 10 cm.
- *Width at node*.—Approximately 13 mm.
- *Cross section*.—Circular.
- *Surface texture*.—Striated.
- *Main color*.—About Light Greyed-Orange 171D.
- *Color of dorsal side of internode*.—Mainly about Light Greyed-Orange 171D.
- *Color of ventral side of internode*.—Mainly about Light Greyed-Orange 171D.
- *Color of dorsal side of node*.—Mainly about Medium Greyed-Orange 172B.
- *Color of ventral side of node*.—Mainly about Light Greyed-Orange 171D.
- *Density of erect hairs on nodes*.—Absent or Very Sparse.
- *Density of erect hairs on internodes*.—Absent or Very Sparse.
- *Density of prostrate hairs on internodes*.—Absent or Very Sparse.
- *Density of prostrate hairs on nodes*.—Absent or Very Sparse.

Tendrils:

- *Distribution on the shoot at full flowering*.—Discontinuous.
- *Thickness*.—About 4 mm.
- *Color*.—About Light Yellow-Green 18D in mid-summer.
- *Form*.—Bifurcated.
- *Number of consecutive tendrils*.—Up to 2.
- *Length of tendril*.—Medium, approximately 15 cm.

LEAVES

Young leaves:

- *Color of upper surface of first 4 distal unfolded leaves*.—About Medium Green 138A.
- *Average intensity of anthocyanin coloration of six distal leaves prior to flowering*.—Absent.
- *Density of prostrate hairs between veins at lower surface of 4th distal unfolded leaf*.—Absent or very sparse.
- *Density of erect hairs between veins at lower surface of 4th distal unfolded leaf*.—Absent or very sparse.
- *Density of prostrate hairs on veins at lower surface of 4th distal unfolded leaf*.—Absent or very sparse.
- *Density of erect hairs on veins at lower surface of 4th distal unfolded leaf*.—Absent or very sparse.

Mature leaves (observations made in the middle third of shoot):

- *Average length*.—Medium, approximately 9 cm.
- *Average width*.—Medium, approximately 12 cm.
- *Shape of blade*.—Pentagonal.
- *Number of lobes*.—Approximately 5.
- *Profile*.—Undulate.
- *Blistering surface of blade upper surface*.—Absent or very weak.
- *Leaf blade tip*.—In the plane of the leaf.
- *Undulation of margin*.—Slight.
- *Thickness*.—Average typical of *Vitis vinifera* species.
- *Overall shape of teeth*.—Mostly both sides convex.
- *Length of teeth*.—Short, ranging from 2 mm to 5 mm.
- *Ratio length/width of teeth*.—Small.
- *General shape of petiole sinus lobes*.—Half open.
- *Tooth at petiole sinus*.—Absent.
- *Petiole sinus limited by veins*.—Absent.
- *Shape of upper lateral sinus lobes*.—Open.
- *Depth of upper lateral sinuses*.—Medium, approximately 20 mm to 30 mm.
- *Density of prostrate hairs between veins on lower surface of blade*.—Absent to very sparse.
- *Density of erect hairs between veins on lower surface of blade*.—Absent to very sparse.
- *Density of prostrate hairs on main veins on lower surface of blade*.—Absent to very sparse.
- *Density of erect hairs on main veins on lower surface of blade*.—Absent to very sparse.
- *Density of prostrate hairs on main veins on upper surface of blade*.—Absent to very sparse.

*Autumn coloration of leaves*.—Mainly Medium Yellow-Green 144A and Medium Yellow-Green 144B with some mottling of Medium Red 41B and Dark Greyed-Red 182A.

Upper surface:

*Color*.—About Dark Green 135A.

*Surface texture*.—Smooth.

*Surface appearance*.—Dull.

*Anthocyanin coloration of main veins*.—Absent or very sparse.

Lower surface:

*Color*.—About Medium Green 138B.

*Surface texture*.—Smooth.

*Surface appearance*.—Dull.

*Anthocyanin coloration of main veins*.—Absent or very sparse.

Petiole:

*Length of petiole*.—Short, approximately 3 cm to 4 cm.

*Diameter*.—Approximately 4 mm.

*Length of petiole compared to middle vein*.—Much shorter.

*Density of prostrate hairs on petiole*.—Absent.

*Density of erect hairs on petiole*.—Absent.

*Color*.—About Medium Green 138B, becoming Medium Greyed-Red 182B as it ages.

Buds:

*Shape*.—Conical.

*Size*.—Medium, approximately 3 mm wide×4 mm long.

*Position*.—Slightly held out.

*Bud fruitfulness*.—Basal, mostly fruitful $3^{rd}$ to $5^{th}$ bud position.

*Time of bud burst*.—Somewhat early for area of Wasco, Calif. Approximately March 9th.

FLOWERS

General:

*Flower type*.—Fully developed stamen and fully developed gynoecium.

*Position of first flowering node*.—$4^{th}$ to $5^{th}$ node of current season growth.

*Number of inflorescences per shoot*.—Approximately 1 to 2 with an average of 1.8

*Time of full bloom*.—Medium for area of Wasco, Calif. Approximately April 25th.

FRUIT

General:

*Ripening period*.—Early, starting about July $9^{th}$, with mid-ripe about July 14th.

*Use*.—Fresh market.

*Storage quality*.—Good.

Cluster:

*Form*.—Conical. Long-shouldered.

*Cluster size* (*peduncle excluded*).—Large.

*Cluster weight*.—Approximately 700 gm.

*Cluster length* (*peduncle excluded*).—Approximately 21 cm.

*Cluster width*.—Approximately 16 cm.

*Cluster density*.—Medium, loose and full.

*Number of berries*.—Approximately 140 for un-tipped clusters and approximately 100 with normal tipping.

Peduncle:

*Length*.—Medium, approximately 2.5 cm.

*Diameter*.—Approximately 5 mm.

*Lignification of peduncle*.—Weak.

*Color*.—About Medium Green 138B where shaded and about Light Red 42D where well lit.

Berry:

*Size*.—Large.

*Berry weight*.—Approximately natural size averages 6.5 g and about 7.8 g when treated with gibberellic acid.

*Dimensions*.—Longitudinal axis: Approximately 25 mm. Horizontal axis: Approximately 22 mm.

*Uniformity of size*.—Uniform.

*Shape*.—Globose.

*Cross section*.—Circular.

*Skin color* (*without bloom*).—About Dark Red 46B.

*Flesh color*.—About White 155C around perimeter with Medium Yellow-Green 154C near the center. Occasionally center becomes Light Orange-Red 35D as berry ripens.

*Anthocyanin color in flesh*.—Weak.

*Bloom* (*cuticular wax*).—Medium.

*Pedicel thickness*.—Medium approximately 1.7 mm.

*Pedicel length*.—Medium approximately 6 mm.

*Berry separation from pedicel*.—Moderately easy.

*Seed traces*.—Berries contain 1 to 3 Greyed-White (156B) rudimentary soft seed traces per berry.

*Berry firmness*.—Very firm.

*Flesh juiciness*.—Juicy.

*Flesh texture*.—Crisp.

*Particular flavor*.—None.

*Refractometer test*.—About 16 brix.

*Juice pH*.—About 4.4.

*Titratable acidity*.—About 0.46%.

*Brix*.—Acid Ratio: approximately 34.8.

Skin:

*Thickness*.—Medium, about 175 μm.

*Texture*.—Smooth.

*Reticulation*.—Absent.

*Tenacity*.—Tenacious to flesh.

*Tendency to crack*.—Low.

*Sensitivity to sunburn*.—None.

What is claimed is:

1. A new and distinct variety of grapevine as herein illustrated and described.

* * * * *

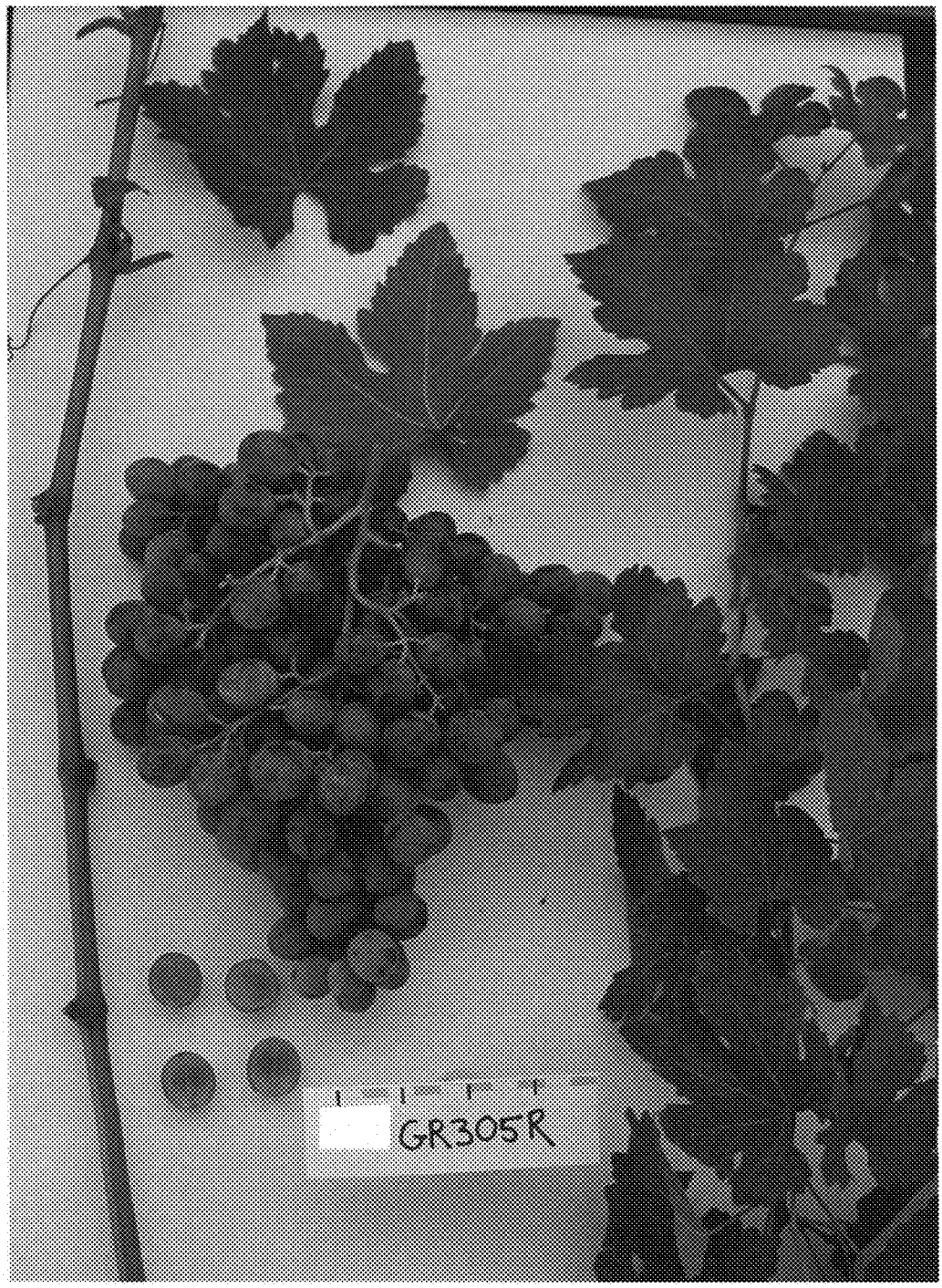
GR305R